United States Patent [19]

Bauman

[11] 4,130,637

[45] Dec. 19, 1978

[54] ANTI-PLAQUE AGENTS

[75] Inventor: Robert A. Bauman, New Brunswick, N.J.

[73] Assignee: Colgate-Palmolive Company, New York, N.Y.

[21] Appl. No.: 839,154

[22] Filed: Oct. 3, 1977

Related U.S. Application Data

[62] Division of Ser. No. 764,122, Jan. 31, 1977, abandoned.

[51] Int. Cl.$^2$ .............................................. A61K 7/22
[52] U.S. Cl. ................................. 424/54; 260/501.13; 424/7; 424/52; 424/57
[58] Field of Search ...................... 260/501.13; 424/54

[56] References Cited

U.S. PATENT DOCUMENTS 3,617,439  11/1971  Chapman .................... 260/501.13 X

OTHER PUBLICATIONS

Swain et al, Journal of Organic Chemistry, 18, 1087–1091 (1953), "Synthesis of N-Alkyldimethyl Derivatives of W-Amino Acids".
Accepted Dental Therapeutics, 35th edition, (1973) RK 701 A3; pp. 60–64, 193–194, 227–236.

*Primary Examiner*—Shep K. Rose
*Assistant Examiner*—Molly C. Eakin
*Attorney, Agent, or Firm*—Robert L. Stone; Murray M. Grill; Herbert S. Sylvester

[57] ABSTRACT

Novel betaine compounds derived from higher alkyl dimethyl carboxylic acid quaternary ammonium compounds; the process of preparing said betaines; and compositions containing an effective antimicrobial amount of said betaines admixed with a pharmaceutical carrier. These compounds are effective in controlling dental plaque without producing an esthetically unacceptable discoloration of tooth surfaces.

9 Claims, No Drawings

ANTI-PLAQUE AGENTS

This is a divisional, of application Ser. No. 764,122 filed Jan. 31, 1977 now abandoned.

Although many quaternary ammonium compounds and other cationic materials such as biguanide salts have been proposed as effective oral antimicrobial and plaque-reducing agents, their extended use in the mouth has been found to result in increased staining of the teeth.

The effective cationic antimicrobials invariably have large hydrophobic groups in the cation and small hydrophilic anions. When these compounds are absorbed onto surfaces such as the teeth, the cations are strongly bound and the anions only lightly bound so that anion exchange can occur freely. The result is similar to the process observed when cations are bonded to polymers to produce the well known anion exchange resins in which anions are more or less readily exchanged depending on the relative affinities of the anions for the immobilized cations. In this way anions which are colored or subject to coloration (for example, by oxidation) may become attached to tooth surfaces and eventually incorporated into calcified deposits. This is one process by which unsightly and difficultly removable stains may appear on the visible tooth surfaces.

It is an advantage of this invention that the anion is made an inseparable part of the molecule and thus not subject to exchange, thereby preventing tooth staining by this mechanism and reducing overall discoloration.

The requirement of a non-exchangeable anion is met by quaternary ammonium compounds which are inner salts and often referred to as betaines or zwitter ionic materials as generalized in the formula $$R_1R_2R_3N^+(CH_2)_nCOO^-$$

Although any compound conforming to this Zwitter ionic structure will have a non-exchangeable anion, it is by no means true that it will also show useful antimicrobial activity. For example, the bactericidal activity of the betaine $C_{16}H_{33}N^+(CH_3)_2 CH_2COO^-$ is reported to be less than one-tenth that of the related non-betaine $[C_{16}H_{33}N(CH_3)_2CH_2C_6H_5]Cl$ by R. L. Stedman, S. L. Engel and I. M. Bilse, J. Appl. Microbiol. 1, 142 (1953).

It has, however, now been discovered that if the carboxylate group is separated from the quaternary nitrogen by as many as ten methylene groups as in $C_{16}H_{33}N^+(CH_3)_2(CH_2)_{10}COO^-$, the activity is not diminished and is sufficient for the exhibition of useful antimicrobial and anti-plaque properties.

Hexadecyldimethyl(10-carboxydecyl)ammonium bromide was prepared by A. P. Swain, D. F. Braun and S. K. Naegele, J. Org. Chem. 18, 1087 (1953) and reported to have antimicrobial properties which are more fully described in the abovementioned publication by Stedman et al. No mention is made of either preparing or evaluating the corresponding betaine, hexadecyldimethyl(10-carboxydecyl)ammonium hydroxide, inner salt.

In accordance with instant invention, it has been found that the butaine and the corresponding carboxylic acid quaternary bromides are equally effective as antimicrobials, and prevent the growth of dental plaque in vivo. However, the presence of the betaine eliminates the objectionable increase in staining associated with quaternary ammonium compounds. This may be as a result of interference with the ion exchange mechanism of staining as outlined above or as a result of some other as yet unknown action.

Accordingly, it is an object of this invention to provide non-staining antimicrobial agents which will inhibit the accumulation of dental plaque.

Another object of this invention is to provide the inner salts (betaines) of quaternary ammonium antimicrobial agents as anti-plaque agents without causing the staining on tooth surfaces associated with the prolonged use of such cationic agents.

Accordingly, the present invention relates to non-staining oral compositions and to novel betaines represented by the general formula:

$$RN^+(CH_3)_2(CH_2)_nCOO^-,$$

wherein R is a higher alkyl group containing 12–18 carbon atoms and preferably 14–16 carbon atoms and n is the integer 8–12. These betaines may be used per se or in combination with the quaternary ammonium compounds from which they are derived, the amount of the betaine constituting at least 50% of the mixture. Compounds where the R has less than 12 carbons and the n is less than 8 possess substantially no antimicrobial activity. Oral compositions containing said betaine compounds per se or in admixture with their corresponding quaternary compound produce less stain on exposure to food or beverages (e.g. coffee, tea, wine, soy sauce) then quaternary compounds of comparable anitmicrobial activity. They cause no objectionable stain under use conditions, whereas other cationics such as benzethonium chloride or chlorhexidine cause noticeable discolorations.

The method of preparing the non-staining betaines of instant invention generally comprises reacting a $C_{12}$–$C_{18}$ alkyl dimethyl amine with a halo-$C_8$–$C_{12}$ alkane carboxylic acid or a halo-$C_8$–$C_{12}$ alkane carboxylic acid ester of 1–8 carbons, and converting the resultant quaternary ammonium compound to the corresponding betaine (inner salt) by hydrolysis, preferably in the presence of a suitable solvent, containing a sufficient amount of alkali hydroxide to convert the carboxylic acid quaternary compound to the corresponding betaine.

It is preferred to utilize about 1.3 to 2 equivalents of an alkali hydroxide such as KOH, NaOH or $NH_4OH$. The solvent utilized during hydrolysis is preferably a lower alcohol such as methanol, ethanol, propanol, butanol, pentanol, and hexanol.

Another method of converting the quaternary ammonium compound in the carboxylic acid form to the corresponding betaine comprises contacting a solution of the former with an anion exchange resin containing exchangeable hydroxide ions, whereby the halide ions are replaced by hydroxide ions. Upon evaporation of the solution obtained by hydrolysis or by anion-exchange, the dried residue is found to be the inner salt of the quaternary ammonium hydroxide. It may be purified by recrystallization from water, acetonitrile, or other suitable medium such as the lower alkanols, i.e. methanol, ethanol, propanol, butanol, pentanol or hexanol.

The quaternization reaction (i.e. the reaction between the tertiary amine and the halocarboxylic acid or the ester thereof) may be conducted in the absence or presence of a suitable organic solvent and at elevated temperatures, preferably at the boiling point of said solvent, and for a sufficient period of time to complete the reaction, from about 6 hours to 72 hours or even longer if necessary. Suitable solvents include propanol, butanol, ethoxyethanol, ethanol, methanol and the like. When no solvent is utilized, a temperature of about 100° C. is preferred.

The following examples illustrate the manner in which compounds of this invention are prepared:

EXAMPLE 1

Preparation of N-(10-Carboxydecyl)-N, N-dimethyltetradecanaminium hydroxide, inner salt (betaine),

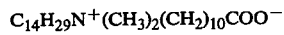

A mixture of 10g (38 mmoles) 11-bromoundecanoic acid, 9.1g (38 mmoles) dimethyltetradecylamine, and 6.0g (57 mmoles) sodium carbonate in 75ml methanol was stirred and refluxed for 65 hours. The residue after evaporation in vacuum was dissolved in 125 ml water, filtered, and acidified to pH 2 with hydrobromic acid. This precipitated tetradecyldimethyl(10-carboxydecyl)-ammonium bromide which, after drying, was recrystallized first from acetone and then from benzene containing about 5% ethanol. The melting point was 129°–130.5° C. The infrared spectrum shows carbonyl absorption at $5.79\mu$ only, which is typical of the free carboxylic acid group. A 2% solution of this carboxylic acid quaternary compound in methanol was passed through a column of anion exchange resin in the hydroxide form (Dowex 1-X8). The betaine recovered by evaporation of the eluate and recrystallization from water and then acetonitrile had a melting point of 190°–192° C. The infrared spectrum shows carbonyl absorption at $6.31\mu$ only, which is typical of the carboxylate ion and substantiates that the compound is indeed a betaine.

Analysis of the quaternary compound and the derived betaine are as follows:

|  | Quaternary Compound | | Betaine | |
|---|---|---|---|---|
|  | Calculated | Found | Calculated | Found |
| % Br: | 15.77 | 15.72 |  |  |
| Equivalent Weight: | 506.6 | 502.6 | 425.7 | 428.8 |

EXAMPLE 2

The procedure of Example 1 was repeated but hexadecyldimethylamine was substituted for the tetradecyldimethylamine. Analysis of the resultant quaternary and betaine is as follows:

|  | 10-Carboxydecyl hexadecyl dimethyl ammonium bromide | | Corresponding Betaine | |
|---|---|---|---|---|
|  | 136 – 138° C | | 195 – 197° C | |
| Melting Point | Calc. | Found | Calc. | Found |
| % Br | 14.94 | 14.98 |  |  |
| Equiv. Wt. | 534.7 | 533.6 | 453.8 | 445.0 |

EXAMPLE 3

A mixture of 24g (100 mmoles) dimethyltetradecylamine and 28g (100 mmoles) methyl 11-bromoundecanoate was heated together at 95°–100° C. for 6.5 hours. At this point, titration of a sample indicated that quaternization was 91% complete. The solidified product was triturated with ether, filtered, dried and recrystallized from ethyl acetate and acetone. The melting point of the tetradecyldimethyl(10-methoxycarbonyldecyl)ammonium bromide was 62–65° C.

The ester quaternary (10.4 g, 20 mmoles) was converted to the betaine by dissolving in a warm solution of 3.0g of 50% sodium hydroxide (38 mmoles) in 50 ml of alcohol. The solution was evaporated to dryness in vacuum and the residue recrystallized from water, acetonitrile, and aqueous acetone. Equivalent weight: Calculated 425.7, Found 430.2

The two processes described in Example 1 and Example 3 may be varied by using other suitable solvents for the quaternization step such as ethanol, butanol, ethoxyethanol, propanol and the temperature varied according to the boiling point of the solvent used. Similarly other alkaline materials may be used to hydrolyze the quaternary compound into its corresponding betaine such as KOH and $NH_4OH$. Other higher alkyl analogs of the dimethyl carboxydecyl ammonium hydroxide betaines may be prepared by using different tertiary amine reactants, such as dodecyldimethylamine, pentadecyldimethylamide, tridecyldimethylamine, octadecyldimethylamine. Similarly, other halo-carboxylic acid reactants may be used such as 11-chloroundecanoic acid, 9-bromo- or chlorononanoic acid, 10-bromo- or chlorodecanoic acid, 12-bromo- or chlorododecanoic acid, 13-bromo- or chlorotridecanoic acid, as well as other carboxylic acid esters thereof such as the ethyl, propyl, butyl, pentyl, hexyl, heptyl or octyl esters.

The compounds of this invention may be used in dental creams, mouthrinses or tooth powders at concentrations of preferably 0.05 to 1.0% and in the pH range of 4 to 9, in which they exist as betaines or mixtures of carboxylic acid quaternary compounds and betaines. It has been found that a 0.2% aqueous solution of the carboxylic acid quaternary compound exhibits a pH of 3.1, and when completely neutralized to the betaine exhibits a pH of 8.7. By titrating the carboxylic acid quaternary compound with NaOH, a 1:1 mixture of the carboxylic acid quaternary compound and betaine is obtained at a pH of 4.2; and at a pH of 6.3, 90% betaine is present. At a pH of 7, about the pH found in the oral cavity, the compound is therefore, substantially all in the betaine form. Accordingly, although the compounds of this invention may be applied as a mixture of betaine and carboxylic acid quaternary compound, when it enters the oral cavity it is converted to substantially all betaine with its concomitant non-staining property.

It has been observed that the betaines generally described in the foregoing formula prevent the growth of dental plaque in vivo and are equally effective antimicrobials as their corresponding carboxylic acid quaternary compounds. More specifically they are particularly effective against gram positive organisms such as *Staphylococcus aureus, Streptococcus sanguis* and *mutans* and *Actinomycetis naeslundii;* gram negative organisms such as *Pseudomonas aeruginosa* and *Escherichia coli;* and against fungi, such as *Candida albicans* (yeast) and *Trichophyton mentogrophytes* and *Aspergillus niger* (mold). An essential advantage of instant betaines is that they are non-staining to oral surfaces as opposed to quaternary compounds of comparable antimicrobial activity.

The antimicrobial nature of the instant novel non-toxic compounds was shown by a standard test tube serial dilution test in which an appropriate number of test tubes of broth containing decreasing concentration of the test agent was innoculated with the test organism (0.1% in 95% ethyl alcohol). After a suitable period of incubation, the tubes were examined for the presence or absence of growth. The activity of the test agent was the lowest concentration which inhibited the growth of the organism and is expressed as the minimal inhibitory concentration in μgm/ml. As shown in the following table of anitmicrobial data, the betaines of this invention are active against a variety of micro-organisms with maximum activity when the higher alkyl group has 14–16 carbons.

TABLE I

| [RN$^+$ (CH$_3$)$_2$(CH$_2$)$_{10}$COOH] | Minimum Inhibitory Concentration (μgm/ml) | | | | | | | | |
|---|---|---|---|---|---|---|---|---|---|
| | Pr$^-$ | Gram Positive | | | Gram Negative | | Yeast | old | |
| R | S. aureus | Strep. mutans | Strep. sanguis | A. naeslundi | E. Coli | Ps. aeruginosa | C. albicans | T. ment. | A. niger |
| C$_{16}$H$_{33}$ | 0.39 | 1.56 | 1.56 | 0.78 | 100 | 50 | 3.12 | 12.5 | 50 |
| C$_{14}$H$_{29}$ | 0.39 | 1.56 | 1.56 | 0.39 | 100 | 50 | 3.12 | 3.12 | 25 |
| C$_{12}$H$_{25}$ | 6.25 | 12.5 | 12.5 | 12.5 | 100 | 50 | 25 | 12.5 | 50 |
| RN$^+$(CH$_3$)$_2$(CH$_2$)$_{10}$COOH | | | | | | | | | |
| C$_{14}$H$_{29}$ | 1.56 | 1.56 | 1.56 | 0.39 | 100 | 100 | 3.12 | 0.78 | 50 |
| C$_{16}$H$_{33}$ | 1.56 | 1.56 | 0.78 | 0.78 | 100 | 100 | 3.12 | 1.56 | 100 |
| Benzethonium Chloride | 0.78 | 0.78 | 3.12 | 0.39 | 100 | 50 | 1.56 | 12.5 | 50 |

These dilution tests evidence the effectiveness of the betaines of the invention against bacteria and fungi in comparison with the corresponding quaternary ammonium compounds. The antimicrobial effectiveness of instant novel compounds also favorably compare to benzethonium chloride, a known and commonly used antimicrobial agent.

An essential feature of instant betaines is their non-staining property, a common disadvantage associated with the use of quaternary compounds.

This reduction in stain formation is clearly evidenced by in vivo tests on beagles, using the method of spraying a 0.1% aqueous test solution into the animal's mouth and immediately after spraying keeping the mouth closed for 1 minute to allow the solution to remain in contact with the oral surfaces and minimize rapid clearance. This treatment was continued daily for 7 weeks. Using 10 dogs, the deionized water treatment gave a Mean Stain Result of 0.07, whereas 0.1% benzethonium chloride gave a Mean Stain Result of 0.59 which represents a 742% increase in staining. Score results range from 0 to 4:

0 nc stain;
1 stain present covering one-fourth of tooth surface;
2 stain present covering one-half of tooth surface;
3 stain present covering three-fourths of tooth surface;
4 stain present covering entire tooth surface.

The animals used in these studies were registered Beagle dogs 6 to 8 months of age, weighing 8 to 10 kilos. The animals were kept in good health and had not received any treatment for at least three weeks prior to the start of a study. They were anaesthesized (Na-Nembutal 25–30 mgs/kg) and received a complete dental prophylaxis. Disclosing solution (TRACE, Erythrosine, Lorvic St. Louis, Mo. U.S.A.) was used to insure the complete removal of soft and hard dental deposits. The dogs receive this diet exclusively — ground Purina Dog Chow soaked in water for at least two hours to form a soft mush. In addition, each animal receives approximately one-half can of ground beef (no chunks). No hard substances were permitted for the duration of the study. The animals were treated once daily with the test solutions (approx. 6 to 9 ml.) using a gentle spray over all surfaces of dentition. Treatments continued at least five days per week for the duration of the experiment. Each animal was examined weekly for plaque, and stain. Photographs were taken by the examining investigator immediately after the prophylaxis and at every examination. Before starting with the plaque study, the groups were balanced with respect to plaque formation.

Using a disclosing solution (a dye which discloses the presence of plaque by coloring the plaque) to measure the extent of plaque coverage on the dental surface, the following Mean Score results were obtained within the range of 1–4, by visual evaluation of 20 teeth per beagle and taking the mean value for all the teeth for all the dogs tested wherein a score of 1 represents plaque on one-fourth of the tooth surface, 2 represents one-half tooth surface, 3 represents three-fourths tooth surface covered and 4 representing entire tooth surface covered.

TABLE II

| | | | PLAQUE | | | |
|---|---|---|---|---|---|---|
| Test Solution | No. of dogs | w. Stain | Mean Stain Score | Mean Score | % Diff. | Signif. |
| Placebo | 8 | 1/8 | 0.388 | 2.19 | | |
| C$_{16}$H$_{33}$N$^+$(CH$_3$)$_2$(CH$_2$)$_{10}$COO$^-$ | | | | | | |
| 50% betaine 50% quat. pH 4.3 | 7 | 2/7 | 0.431 | 1.78 | −18.7 | N.S. |
| 90% betaine pH 6.3 | 8 | 1/8 | 0.22 | 1.90 | −21.0 | 95% |
| Hibitane pH 5.0 (Chlorhexidine) | 8 | 8/8 | 0.956 | 1.32 | −39.7 | 95% |
| .075% benzethonium chloride | 7 | 3/7 | 0.53 | 1.80 | −25.0 | 99% |

These results clearly show that all the test solutions reduced plaque compared to the placebo, but that the betaine compounds of this invention exhibited the lowest degree of staining. Hibitane significantly increased staining with 8/8 dogs having cosmetically unacceptable stain, and the 50/50 quaternary ammonium compound and betaine mixture exhibited a moderate degree of staining but significantly less then either the Hibitane or the benzethonium chloride (both being prior art antiplaque agents).

The results set forth above indicate the significant effectiveness of the betaines and mixtures thereof with their corresponding carboxylic acid quaternary compounds as non-staining anti-plaque agents in oral compositions. Since there is a relationship between plaque accumulation and gingivitis in humans, and since beagle studies have shown a positive relationship between the amount of soft dental deposits and the severity of gingivitis, these results are significant in the formulation of an oral preparation capable of reducing plaque formation and preventing gingivitis.

When used against bacteria or fungi, compounds of the instant invention may be applied directly to the surface to be protected or may be dissolved in a pharmaceutical carrier. Typically, an effective amount, e.g., 0.025 to about 10% by weight of the compound, is included in an inert carrier and a dispersing or surface-active agent. Alternatively, an effective amount, e.g., 0.025 to about 10% by weight may be incorporated into a solid carrier which may be inert, such as talc, clay, diatomaceous earth, flour, etc.

When compounds of the instant invention are intended for use in compositions which inhibit the formation of oral plaque, they are typically incorporated in oral preparations in effective amounts up to about 5% by weight, preferably 0.05–1% by weight of the oral preparation. Typically, the oral preparation is a dentifrice, such as dental cream, tablet or powder, containing as a vehicle about 20–95% by weight of a water-insoluble polishing material, preferably including water-insoluble phosphate such as dicalcium phosphate, tricalcium phosphate, trimagnesium phosphate. The dentifrice may also include water; binders such as glycerine, sorbitol, propylene glycol 400; detergents; gelling agents such as Irish moss and sodium carboxy methyl cellulose; additional antibacterial agents; coloring or whitening agents; preservatives; silicones; chlorophyll compounds, additional ammoniated materials; flavoring or sweetening materials; and compounds which provide fluorine-containing ion such as sodium fluoride, stannous fluoride and sodium nonfluorophosphate.

The oral preparation may also be a liquid such as mouth rinse which typically contains 20–99% by weight of an aqueous lower aliphatic alcohol, preferably having about 1–30% by weight alcohol such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE 4

| Dental Cream | % |
|---|---|
| N-(10-Carboxydecyl)-N,N-dimethyltetradecanaminium hydroxide, inner salt | 0.50 |
| Nonionic detergent* | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |
| Dicalcium phosphate dihydrate | 46.75 |
| Flavor | 0.80 |
| Water | 22.15 |
| pH 7.0 | |

*Tween 80-Polyoxyethylene (20 moles ethylene oxide) sorbitan monooleate.

EXAMPLE 5

0.50% of the betaine-N-(10-Carboxydecyl)-N,N-dimethylhexadecanaminium hydroxide, inner salt was used in lieu of the betaine in Example 4.

EXAMPLE 6

0.50% of a 9:1 mixture of the betaine of Example 4 and its corresponding carboxylic acid quaternary, (*), was used in lieu of the betaine of Example 4. pH 6.3

*Tetradecyldimethyl(10-Carboxydecyl)ammonium bromide

EXAMPLE 7

Mouthwash

A 9:1 mixture of the betaine of Example 2 and its corresponding carboxylic acid quat.

| | % |
|---|---|
| Hexadecyldimethyl(10-Carboxydecyl)ammonium bromide | 0.025 |
| Nonionic detergent (pluronic F-68)* | 1.00 |
| Ethyl alcohol (containing flavor) | 15.00 |
| Glycerine | 10.00 |
| Saccharin | 0.02 |
| Water | 73.955 |
| pH 6.3 | |

*Block polymer of 80% polyoxyethylene and 20% polyoxypropylene.

EXAMPLE 8

0.05% of the betaine of Example 1 or a mixture of the betaine and its corresponding Carboxylic acid quaternary compound at a pH of 4.3 was substituted for the betaine of Example 7 and the water content was adjusted accordingly.

EXAMPLE 9

0.05% of the betaine of Example 2 or a mixture of the betaine and its corresponding Carboxylic acid quaternary salt at a pH of 4.3 was used in lieu of the betaine of Example 7.

EXAMPLE 10

0.05% of -N-(10-Carboxydecyl)-N,N-dimethyldodecanaminium hydroxide, inner salt or in admixture with the corresponding bromide quaternary salt at a pH of 7.0, was used in lieu of the betaine of Example 7.

A preferred ingredient of instant composition is a nonionic organic surfactant which provides increased prophylactic action, assists in achieving thorough and complete dispersion of instant compositions throughout the oral cavity and renders instant compositions more cosmetically acceptable. The non-ionic surfactant imparts to the composition, detersive and foaming properties as well as maintains the flavoring materials in solution (i.e. solubilizes flavor oils). In addition, the non-ionics are completely compatible with the compounds of this invention, thereby providing for a stable, homogeneous composition of enhanced anti-bacterial, and anti-plaque activity.

The nonionic organic surface compounds which are contemplated are commercially known and comprise the water-soluble products which are derived from the condensation of an alkylene oxide or equivalent reactant and a reactive-hydrogen hydrophobe. The hydrophobic organic compounds may be aliphatic, aromatic or heterocyclic, although the first two classes are preferred. The preferred types of hydrophobes are higher aliphatic alcohols and alkyl phenols, although others may be used such as carboxylic acids, carboxamides, mercaptans, sulphonamides, etc. The ethylene oxide condensates with higher alkyl phenols represent a preferred class of nonionic compounds. Usually the hydrophobic moiety should contain at least about 6 carbon atoms, and preferably at least about 8 carbon atoms, and may contain as many as about 50 carbon atoms or more. The amount of alkylene oxide will vary considerably depending upon the hydrophobe, but as a general guide and rule, at least about 5 moles of alkylene oxide per mole of hydrophobe should be used. The upper limit of alkylene oxide will vary also, but no particular criticality can be ascribed thereto. As much as 200 or more moles of alkylene oxide per mole of hydrophobe may be employed. While ethylene oxide is the preferred and predominating oxyalkylating reagent, other lower alkylene oxides such as propylene oxide, butylene oxide, and the like may also be used or substituted in part for the ethylene oxide. Other nonionic compounds which are suitable are the polyoxyalkylene esters of the organic acids such as the higher fatty acids, the rosin acids, tall oil acids, acids from petroleum oxidation products, etc. These esters will usually contain from about 10 to about 22 carbon atoms in the acid moiety and from about 12 to about 30 moles of ethylene oxide or its equivalent.

Still other nonionic surfactants are the alkylene oxide condensates with the higher fatty acid amides. The fatty acid group will generally contain from about 8 to about 22 carbon atoms and this will be condensed with about 10 to about 50 moles of ethylene oxide as the preferred illustration. The corresponding carboxamides and sulphonamides may also be used as substantial equivalents.

Still another class of nonionic products are the oxyalkylated higher aliphatic alcohols. The fatty alcohols should contain at least 6 carbon atoms, and preferably at least 8 carbon atoms. The most preferred alcohols are lauryl, myristyl, cetyl, stearyl and oleyl alcohols and the said alcohols should be condensed with at least about 6 moles of ethylene oxide, and preferably about 10 to 30 moles of ethylene oxide. A typical nonionic product is oleyl alcohol condensed with 15 moles of ethylene oxide. The corresponding alkyl mercaptans when condensed with ethylene oxide are also suitable in the compositions of the present invention.

The amount of non-ionic may generally be varied from about 0.2–3.0% by weight of the total formulation, depending on the specific nature of the non-ionic utilized as well as on the amounts and nature of the other ingredients in the oral formulation.

Although this invention has been described with reference to specific examples, it will be apparent to one skilled in the art that various modifications may be made thereto which fall within its scope.

I claim:

1. A non-staining, anti-plaque oral composition containing an effective antimicrobial amount of a betaine represented by the general formula:

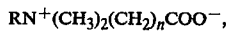

$$RN^+(CH_3)_2(CH_2)_nCOO^-,$$

wherein R is an alkyl group containing 12 to 18 carbon atoms and n is an integer from 8 to 12, in an oral vehicle.

2. A composition in accordance with claim 1, wherein the betaine is -N-(10-Carboxydecyl)-N,N-dimethyltetradecanaminium hydroxide, inner salt.

3. A composition in accordance with claim 1, wherein the betaine is -N-(10-Carboxydecyl)-N,N-dimethylhexadecanaminium hydroxide, inner salt.

4. A composition in accordance with claim 1, wherein the composition has a pH of 4 to 9.

5. A composition in accordance with claim 4, wherein the betaine exists as a mixture of at least 50% betaine and its corresponding carboxylic acid quaternary compound.

6. A composition in accordance with claim 5, wherein the betaine constitutes about 0.025 to 10% by weight of the compound in an inert pharmaceutical carrier.

7. A composition in accordance with claim 5, wherein the betaine constitutes about 0.05 to 5.0% by weight in a dental vehicle containing about 20–95% by weight of water-insoluble polishing material.

8. A composition in accordance with claim 5, wherein the betaine constitutes about 0.025 to 10% by weight in a dental vehicle containing about 20–99% by weight of an aqueous lower aliphatic alcohol.

9. A composition in accordance with claim 5, wherein the oral vehicle contains about 0.2–3.0% by weight of a non-ionic surfactant.

* * * * *